United States Patent [19]

Taglieber et al.

[11] Patent Number: 4,929,758

[45] Date of Patent: May 29, 1990

[54] PREPARATION OF TERT-BUTYLAMINE FROM ISOBUTENE

[75] Inventors: Volker Taglieber, Eppelheim; Wolfgang Hoelderich, Frankenthal; Rudolf Kummer, Frankenthal; Wolf D. Mross, Frankenthal; Guenter Saladin, Ludwigshafen, all of Fed. Rep. of Germany

[73] Assignee: BASF Aktiengesellschaft, Ludwigshafen, Fed. Rep. of Germany

[21] Appl. No.: 212,161

[22] Filed: Jun. 13, 1988

Related U.S. Application Data

[63] Continuation of Ser. No. 908,297, Sep. 17, 1986, abandoned, which is a continuation-in-part of Ser. No. 663,283, Jul. 23, 1984, abandoned.

[30] Foreign Application Priority Data

Jul. 23, 1983 [DE] Fed. Rep. of Germany ....... 3326579

[51] Int. Cl.$^5$ ..................... C07C 85/02; C07C 85/18
[52] U.S. Cl. .................................................. 564/485
[58] Field of Search ..................... 564/408, 445, 485

[56] References Cited

U.S. PATENT DOCUMENTS

| | | | |
|---|---|---|---|
| 4,208,305 | 6/1980 | Konvenhoven et al. | 556/173 |
| 4,307,250 | 12/1981 | Peterson et al. | 564/485 |
| 4,427,577 | 1/1984 | Koetsier | 502/74 |
| 4,431,746 | 2/1984 | Rollman | 502/77 |

OTHER PUBLICATIONS

Kokotailo et al., "The Properties and Applications of Zeolites", *Special Pub. of Chem. Soc. of London #33*, (1979).

Gabelicq et al.: *Chemical Abstracts*, vol. 98: 114326q (1983).

*Primary Examiner*—Douglas W. Robinson
*Assistant Examiner*—K. Weddington
*Attorney, Agent, or Firm*—Keil & Weinkauf

[57] ABSTRACT

Amines are prepared from an olefin and ammonia or a primary and/or secondary amine in the presence of a zeolite catalyst of the pentasil type. Iron silicate zeolites of the pentasil type having an $SiO_2/Fe_2O_3$ ratio greater than or equal to 10 are preferably used.

7 Claims, No Drawings

PREPARATION OF TERT-BUTYLAMINE FROM ISOBUTENE

This application is a continuation of application Ser. No. 908,297, filed on Sept. 17, 1986 now abandoned, which is a continuation-in-part of Ser. No. 663,283 filed 7/23/84 now abandoned.

The present invention relates to a process for the preparation of amines by an addition reaction of ammonia, or of an amine which reacts in a similar manner, with an olefin.

The addition reaction of ammonia, or of an amine which reacts in a similar manner, with an olefin has long been known and has frequently been described. To date, the reaction has not been realized industrially since the conventional processes give inadequate selectivities and/or catalyst lives, as described in, for example, U.S. Pat. Nos. 2,623,061, 2,422,631, 2,501,556 and 3,412,158. The process described in U.S. Pat. No. 4,307,250 also cannot be carried out on an industrial scale. The Y-type aluminosilicate zeolites which are used as catalysts promote substantial polymer formation and subsequent coking, which results in rapid deactivation of the catalyst.

We have found that, in the preparation of amines from an olefin and ammonia or primary and/or secondary amines at from 80° to 400° C. and under from 40 to 700 bar, the catalyst used has a long life and high selectivity if an olefin is reacted with ammonia or primary and/or secondary amines, or a mixture of these, in the presence of a zeolite catalyst of the pentasil type, the resulting amine is isolated and the unreacted starting materials are recycled.

A further feature of the novel process is that evan a small excess of ammonia or amine is sufficient to give the desired product with high selectivity and to avoid dimerization and/or oligomerization of the olefin used.

Particularly good results are obtained if the catalyst used is an iron silicate zeolite of the pentasil type having an $SiO_2/Fe_2O_3$ ratio greater than or equal to 10.

In an embodiment of the process, ammonia and/or the amines are mixed with the olefin in a molar ratio of from 1:1 to 5:1, and the mixture is fed to a fixed bed or fluidized bed reactor and reacted under from 40 to 700, in particular from 200 to 300, bar and at from 80° to 400° C., in particular from 250° to 350° C., in the gas phase or in a supercritical state. In another embodiment, the reaction is carried out in the liquid phase under from 40 to 80 bar and at from 60° to 120° C. in a stirred kettle, a solid/liquid fluidized bed or a flow tube. The desired product is obtained from the reaction mixture by a conventional method, for example distillation or extraction, and, if necessary, is brought to the desired purity by further separation operations. The unreacted starting materials are recycled to the reactor.

Monounsaturated or polyunsaturated olefins at 2 to 10 carbon atoms, or mixtures of these, can be used as starting materials. Because of the lower tendency to undergo polymerization, monoolefins are more suitable than diolefins or polyolefins, although these can also be reacted selectively with the aid of a larger excess of ammonia or amine. The position of the equilibrium, and hence the conversion to the desired amine, depends to a very great extent on the reaction pressure chosen. High pressure favors the adduct, but, for technical and economic reasons, the optimum pressure is no higher than 300 bar. Apart from being affected by factors such as the excess amount of ammonia or amine, and the catalyst, the selectivity of the reaction is influenced to a large extent by the temperature. Although the rate of the addition reaction increases sharply with increasing temperature, competing crack and recombination reactions of the olefin are promoted at the same time. The optimum temperature with regard to conversion and selectivity depends on the constitution of the olefin, of the amine employed and of the catalyst, and is in general from 250° to 350° C. The residence time depends on the starting materials, and is advantageously from a fraction of a second to a few minutes.

The catalysts used for the amination of olefins are zeolites of the pentasil type. These can have different chemical compositions and may be, for example, iron silicate, gallium silicate, chromium silicate, arsenosilicate or bismuth silicate zeolites or mixtures of these, or aluminogermanate, gallium germanate or iron germanate zeolites or mixtures of these.

The iron silicate zeolites are particularly useful. Suitable iron silicate zeolites are obtained, for example, from an iron compound, preferably $Fe_2(SO_4)_3$, and a silicon compound, preferably higher disperse silicon dioxide, in an aqueous solution of an amine, in particular in a solution of hexane-1,6-diamine, propane-1,3-diamine or triethylenetetramine, with or without the addition of an alkali metal or alkaline earth metal, at from 100° to 220° C. under autogenous pressure.

Suitable iron silicate zeolites can also be synthesized in an ether medium, such as diethylene glycol dimethyl ether, in an alcoholic medium, such as methanol or butane-1,4-diol, or in water.

After the resulting, iron silicate zeolites have been isolated, dried at from 100° to 160° C., preferably about 110° C., and calcined at from 450° to 550° C., preferably about 500° C., they can be mixed with a binder in a weight ratio of from 90:10 to 40:60 and then converted to extrudates or tablets. Suitable binders are various aluminas, preferably boehmite, amorphous aluminosilicates having an $SiO_2/Al_2O_3$ ratio of from 25:75 to 95:5, preferably 75:25, silicon dioxide, preferably higher disperse $SiO_2$, mixtures of highly disperse $SiO_2$ and highly disperse $Al_2O_3$, highly disperse $TiO_2$, and clay. After the molding procedure, the extrudates or pellets are advantageously dried at 110° C. for 16 hours and calcined at 500° C. for 16 hours.

In a particular embodiment, the iron silicate zeolite isolated is molded directly after the drying procedure, and is subjected to calcination only after molding has been carried out.

By milling and sieving the catalyst extrudates, it is possible to obtain fluidizable material from 0.1 to 0.8 mm in size.

When the zeolite catalyst has been deactivated by coking during the reaction according to the invention, the catalyst can be regenerated in a simple manner by burning off the coke deposit in air or in an air/$N_2$ mixture at from 400° to 550° C., preferably about 500° C. As a result of this procedure, the catalyst regains its initial activity.

To increase the selectivity, the catalyst life and the number of regenerations possible, the zeolite catalysts can be modified in a number of different ways.

In one possible method of modifying the catalysts, the unmolded zeolites or the zeolite moldings are doped or subjected to an ion exchange reaction with an alkali metal, eg. Na or K, an alkaline earth metal, eg. Ca or Mg, an earth metal, eg. Tl, a transition metal, eg. Mn, Fe, Mo, Cu or Zn, or a rare earth metal, eg. La or Ce.

In an advantageous embodiment, the pentasil zeolite moldings are initially taken in a flow tube and, for example, a halide or a nitrate of one of the metals described above is passed over at from 20° to 100° C. Ion exchange of this type can be carried out, for example, on the hydrogen, ammonium or alkali metal form of the zeolite.

Another possible method of introducing the metal onto the zeolite comprises impregnating the zeolite material with, for example, a halide, a nitrate or an oxide of one of the metals described above, in aqueous or alcoholic solution.

Both ion exchange and impregnation can be followed by a drying step and, if desired, repeated calcination. In the case of metal-doped zeolites, after-treatment with hydrogen and/or steam may be advantageous.

Another possible method of modification comprises treating the zeolite material, in either molded or unmolded form, with an acid, eg. hydrochloric acid, hydrofluoric acid or phosphoric acid.

In a particular embodiment, the zeolite powder, before being molded, is refluxed with 0.001–2N, preferably 0.05–0.5N, hydrofluoric acid for from 1 to 3 hours. The product is filtered off, washed, dried at from 100° to 160° C. and then calcined at from 400° to 550° C. Another particular embodiment comprises molding the zeolite together with a binder and then treating the moldings with HCl. In this procedure, the zeolite is treated with from 3 to 25, in particular from 12 to 20, % strength hydrochloric acid for from 1 to 3 hours at from 60° to 80° C., and the product is then washed, dried at from 100° to 160° C. and calcined at from 400° to 550° C.

Another possible method of modification comprises exchange with an ammonium salt, eg. $NH_4Cl$, or with a mono-, di- or polyamine. In this procedure, the zeolite, which has been molded with a binder and is present in the H form or in a different ammonium form, is subjected to continuous exchange with from 10 to 25, preferably 20, % strength $NH_4Cl$ solution for 2 hours at from 60° to 80° C., the weight ratio of zeolite to ammonium chloride solution being 1:15, and the product is then dried at from 100° to 120° C.

For the amination of the olefins, the catalysts can be used in the form of 2–4 mm extrudates, tablets having a diameter of from 3 to 5 mm, fluidizable material from 0.1 to 0.8 mm in size, or grit having a diameter of from 0.5 to 1 mm.

The Examples which follow illustrate this invention.

EXAMPLE 1

Catalyst A is an aluminosilicate zeolite of the pentasil type, which is synthesized from 65 g of highly disperse $SiO_2$ and 20.3 g of $Al_2(SO_4)_3.18H_2O$ in 1 kg of an aqueous hexane-1,6-diamine solution (weight ratio 50:50) in a stirred autoclave under hydrothermal conditions, under autogenous pressure and at 150° C. The crystalline product is filtered off, washed, dried at 110° C. for 24 hours and then calcined at 500° C. for 24 hours. This aluminosilicate zeolite, which contains 91.6% by weight of $SiO_2$ and 4.6% by weight of $Al_2O_3$, is mixed with boehmite in a weight ratio of 60:40, the mixture is converted to 2 mm extrudates and the latter are dried at 100° C. for 16 hours and calcined at 500° C. for 24 hours.

To prepare catalyst B, 50 g of catalyst A are impregnated with 9.39 g of $Zn(NO_3)_2.6H_2O$ dissolved in 20 g of $H_2O$. After impregnation, the product is dried at 130° C. for 2 hours and calcined at 540° C. for 2 hours.

10 ml of catalyst A or B described above are introduced into a 0.3 liter stirred autoclave, the autoclave is closed and the olefins and ammonia or amines are forced in. The amount of starting material is such that the autogenous pressure of the reactants at the reaction temperature chosen corresponds to the desired pressure. The molar ratio of ammonia or amine to olefin is varied from 1:1 to 5:1, and the reaction time is fixed at 30 minutes.

The liquid phase and the gas phase of the reacted mixture are investigated separately by gas chromatography. The conversions shown in Table 1 are based in each case on the olefin; the stated selectivities are based on the principal products: ethylamine from ethylene, isopropylamine from propylene, isobutylamine from but-1-ene, tert.-butylamine from isobutene, isopentylamine from isobutene and methylamine, and 1-amino-4-(1-aminoethyl)-cyclohexane from 4-vinyl-1-cyclohexene.

TABLE 1

| Olefin | Amine | Molar ratio amine:olefin | Catalyst | Temperature (°C.) | Pressure (bar) | Conversion (%) | Selectivity (%) |
|---|---|---|---|---|---|---|---|
| Ethylene | $NH_3$ | 2:1 | A | 350 | 300 | 3.2 | 94.7 |
| Ethylene | $NH_3$ | 2:1 | A | 380 | 305 | 6.5 | 93.3 |
| Ethylene | $NH_3$ | 2:1 | B | 350 | 290 | 4.8 | 95.7 |
| Propylene | $NH_3$ | 2:1 | A | 330 | 285 | 7.3 | 97.3 |
| Propylene | $NH_3$ | 2:1 | A | 350 | 295 | 10.4 | 96.5 |
| Propylene | $NH_3$ | 2:1 | B | 330 | 300 | 8.7 | 97.6 |
| But-1-ene | $NH_3$ | 1.5:1 | A | 300 | 290 | 9.1 | 96.1 |
| Isobutene | $NH_3$ | 1.5:1 | A | 320 | 295 | 10.9 | 97.9 |
| Isobutene | $NH_3$ | 1.5:1 | A | 330 | 590 | 12.1 | 97.4 |
| Isobutene | $NH_3$ | 1.5:1 | B | 330 | 285 | 10.8 | 97.9 |
| Isobutene | $NH_3$ | 1.5:1 | B | 330 | 540 | 11.7 | 96.8 |
| Isobutene | $CH_3NH_2$ | 2:1 | A | 330 | 240 | 7.7 | 91.8 |
| 4-Vinyl-1-cyclohexene | $NH_3$ | 4:1 | A | 330 | 275 | 6.8 | 85.7 |

EXAMPLE 2

Continuous preparation is carried out using a high pressure reactor which has a length of 2 m and an internal diameter of 24 mm, is heated by means of an aluminum block and is equipped for internal temperature measurement at three points and with a pressure regulator. 60 ml of each catalyst are introduced, and the upper part of the reactor tube is filled with porcelain rings. The olefin and amine are fed in from above.

The reacted mixtures are analyzed by gas chromatography and in some cases also by distillation.

The results obtained with catalyst A are shown in Table 2.

TABLE 2

| Olefin | Amine | Molar ratio amine:olefin | Catalyst | Space velocity (kg per liter of catalyst per hour) | Temperature (°C.) | Pressure (bar) | Conversion (%) | Selectivity (%) | STY (kg per liter of catalyst per hour) |
|---|---|---|---|---|---|---|---|---|---|
| Isobutene | NH$_3$ | 1.5:1 | A | 9 | 320 | 300 | 6.6 | 98.7 | 0.33 |
| Isobutene | NH$_3$ | 1.5:1 | A | 9 | 350 | 300 | 8.4 | 97.6 | 0.62 |

STY = space-time yield for tert.-butylamine

EXAMPLE 3

Catalyst C is prepared by molding an iron silicate zeolite together with boehmite in a weight ratio of 60:40 to give extrudates and then calcining the latter at 500° C. for 16 hours. The iron silicate zeolite of the pentasil type is synthesized from 273 g of water glass, dissolved in 253 g of an aqueous hexane-1,6-diamine solution (weight ratio 50:50) and 31 g of iron sulfate, dissolved in 21 g of 96% strength sulfuric acid and 425 g of water, in a stirred autoclave in the course of 4 days under hydrothermal conditions, under autogenous pressure and at 165° C. The product is filtered off, washed, dried at 110° C. for 24 hours and calcined at 500° C. for 24 hours. This iron silicate zeolite has an SiO$_2$/Fe$_2$O$_3$ ratio of 17.7 and contains 0.62% by weight of Na$_2$O.

Catalyst D is obtained by impregnating 50 g of catalyst A with 7.9 g of Mn(NO$_3$)$_2$.4H$_2$O dissolved in 20 g of H$_2$O, and drying the product at 130° C. for 2 hours and calcining it at 540° C. for 2 hours.

In a tube reactor (6 mm internal diameter), a mixture of isobutene and ammonia in a molar ratio of 1:1.3 is converted over the catalysts A, B, C and D under isothermal conditions at 300° C. and under 300 bar, a batchwise procedure being employed. The products are analyzed continuously by gas chromatography. The experimental results are summarized in Table 3.

TABLE 3

| Catalyst | A | B | C | C | D |
|---|---|---|---|---|---|
| Temperature (°C.) | 300 | 300 | 300 | 300 | 300 |
| Pressure (bar) | 300 | 300 | 300 | 300 | 300 |
| GHSV (liter of educt per g of catalyst per hour) | 10 | 5.0 | 11 | 9.5 | 10 |
| Conversion of isobutene (%) | 11.1 | 12.1 | 11.2 | 9.5 | 9.0 |
| Selectivity with respect to tert.-butylamine (%) | 93.6 | 95.2 | 94.9 | 96.0 | 90.1 |

We claim:

1. A process for preparing tert-butylamine from isobutene, which comprises the steps of:
   (a) reacting isobutene with ammonia, or a primary or secondary amine, or a mixture thereof in the presence of an iron silicate catalyst of the pentasil type at from 250°–350° C. and under 200–300 bar;
   (b) isolating the tert-butylamine; and
   (c) recycling unreacted starting materials.

2. The process of claim 1, wherein the catalyst is molded together with a binder and then calcined.

3. The process of claim 1, wherein the catalyst is treated with an acid.

4. The process of claim 1, wherein the catalyst is doped with a transition metal.

5. The process of claim 1, wherein the catalyst is doped with a rare earth.

6. The process of claim 1, wherein the catalyst is doped with at least one of the following: an alkali metal, an alkaline earth metal or an earth metal.

7. The process of claim 1, wherein the catalyst is treated with an ammonium salt and then used in its ammonium form.

* * * * *